US010485442B2

(12) United States Patent
Krueger et al.

(10) Patent No.: US 10,485,442 B2
(45) Date of Patent: Nov. 26, 2019

(54) METHOD AND APPARATUS FOR ENHANCING VENTRICULAR BASED ATRIAL FIBRILLATION DETECTION USING ATRIAL ACTIVITY

(71) Applicant: Cardiac Pacemakers, Inc., St. Paul, MN (US)

(72) Inventors: Jonathan Walter Krueger, New Richmond, WI (US); Deepa Mahajan, Roseville, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 310 days.

(21) Appl. No.: 15/341,565

(22) Filed: Nov. 2, 2016

(65) Prior Publication Data

US 2017/0127965 A1    May 11, 2017

Related U.S. Application Data

(60) Provisional application No. 62/252,014, filed on Nov. 6, 2015.

(51) Int. Cl.
*A61B 5/046* (2006.01)
*A61B 5/00* (2006.01)
(Continued)

(52) U.S. Cl.
CPC .............. *A61B 5/046* (2013.01); *A61B 5/042* (2013.01); *A61B 5/04017* (2013.01);
(Continued)

(58) Field of Classification Search
CPC ... A61B 5/046; A61B 5/0464; A61B 5/04017; A61B 5/686; A61B 5/7282; A61B 5/00; A61N 1/359; A61N 1/362
See application file for complete search history.

(56) References Cited

U.S. PATENT DOCUMENTS

| 5,622,178 A | 4/1997 | Gilham |
| 6,490,479 B2 | 12/2002 | Bock |

(Continued)

FOREIGN PATENT DOCUMENTS

| AU | 2015301633 B2 | 8/2018 |
| CN | 1829554 A | 9/2006 |

(Continued)

OTHER PUBLICATIONS

"U.S. Appl. No. 14/825,669, Response filed Apr. 24, 2017 to Final Office Action dated Mar. 9, 2017", 12 pgs.

(Continued)

*Primary Examiner* — Paula J Stice
(74) *Attorney, Agent, or Firm* — Schwegman Lundberg & Woessner, P.A.

(57) ABSTRACT

An example of a system may include a sensing circuit to sense a cardiac signal indicative of atrial and ventricular depolarizations and an atrial fibrillation (AF) detection circuit to detect AF. The AF detection circuit may include a detector and a detection enhancer. The detector may be configured to detect the ventricular depolarizations using the cardiac signal, measure ventricular intervals, and detect AF using the ventricular intervals. The detection enhancer may be configured to generate atrial detection windows each being a time interval prior to each of the detected ventricular depolarizations, compute an atrial activity score using a rolling average of portions of the cardiac signal within the atrial detection windows, and verify the detection of the AF using the atrial activity score and an atrial activity threshold. The atrial activity score is a measure of consistency between a relationship between the atrial depolarizations and the ventricular depolarizations.

20 Claims, 6 Drawing Sheets

(51) Int. Cl.
    *A61B 5/04*     (2006.01)
    *A61B 5/042*    (2006.01)
    *A61N 1/36*     (2006.01)
    *A61N 1/365*    (2006.01)
    *A61N 1/39*     (2006.01)

(52) U.S. Cl.
    CPC ............ *A61B 5/686* (2013.01); *A61B 5/6869* (2013.01); *A61B 5/7221* (2013.01); *A61B 5/7282* (2013.01); *A61N 1/365* (2013.01); *A61N 1/36114* (2013.01); *A61N 1/36135* (2013.01); *A61N 1/395* (2013.01); *A61N 1/3925* (2013.01); *A61N 1/3956* (2013.01); *A61N 1/3962* (2013.01); *A61N 1/3987* (2013.01)

(56) References Cited

U.S. PATENT DOCUMENTS

| | | |
|---|---|---|
| 6,931,273 B2 | 8/2005 | Groenewegen et al. |
| 7,031,765 B2 | 4/2006 | Ritscher et al. |
| 7,353,057 B2 | 4/2008 | Schiessle et al. |
| 7,412,282 B2 | 8/2008 | Houben |
| 7,596,405 B2 | 9/2009 | Kurzweil et al. |
| 7,657,307 B2 | 2/2010 | Van Dam et al. |
| 7,899,531 B1 | 3/2011 | Benser et al. |
| 8,195,280 B2 | 6/2012 | Van Dam et al. |
| 8,560,058 B2 | 10/2013 | Babaeizadeh et al. |
| 8,639,316 B2 | 1/2014 | Sarkar |
| 9,999,368 B2 | 6/2018 | Perschbacher et al. |
| 2001/0034539 A1 | 10/2001 | Stadler et al. |
| 2002/0065473 A1 | 5/2002 | Wang et al. |
| 2004/0092836 A1 | 5/2004 | Ritscher et al. |
| 2005/0080347 A1 | 4/2005 | Sheth et al. |
| 2006/0247548 A1 | 11/2006 | Sarkar et al. |
| 2007/0100248 A1 | 5/2007 | Van Dam et al. |
| 2008/0161703 A1 | 7/2008 | Houben et al. |
| 2009/0112110 A1 | 4/2009 | Zhang |
| 2010/0057152 A1 | 3/2010 | Kim et al. |
| 2010/0274149 A1 | 10/2010 | Li et al. |
| 2011/0152957 A1 | 6/2011 | Shaquer |
| 2012/0035489 A1 | 2/2012 | Dong et al. |
| 2012/0101541 A1 | 4/2012 | Corbucci et al. |
| 2012/0238891 A1 | 9/2012 | Sarkar et al. |
| 2012/0238892 A1 | 9/2012 | Sarkar |
| 2013/0150911 A1 | 6/2013 | Perschbacher et al. |
| 2016/0045125 A1 | 2/2016 | Krueger et al. |
| 2016/0287115 A1 | 10/2016 | Perschbacher et al. |
| 2018/0242869 A1 | 8/2018 | Perschbacher et al. |

FOREIGN PATENT DOCUMENTS

| | | |
|---|---|---|
| CN | 106659407 A | 5/2017 |
| CN | 107529988 A | 1/2018 |
| EP | 2407097 A1 | 1/2012 |
| JP | 2004524074 A | 8/2004 |
| JP | 2006524106 A | 10/2006 |
| JP | 2008539015 A | 11/2008 |
| JP | 2009089883 A | 4/2009 |
| JP | 2013535236 A | 9/2013 |
| JP | 2017527356 A | 9/2017 |
| JP | 2018511400 A | 4/2018 |
| JP | 6434129 B2 | 11/2018 |
| WO | WO-2006118852 A2 | 11/2006 |
| WO | WO-2013020710 A1 | 2/2013 |
| WO | WO-2016025704 A1 | 2/2016 |
| WO | WO-2016160674 A1 | 10/2016 |
| WO | WO-2017079245 A1 | 5/2017 |

OTHER PUBLICATIONS

"U.S. Appl. No. 14/825,669, Advisory Action dated May 3, 2017", 3 pgs.
"U.S. Appl. No. 14/825,669, Appeal Brief filed Dec. 26, 2017", 17 pgs.
"U.S. Appl. No. 14/825,669, Final Office Action dated Mar. 9, 2017", 13 pgs.
"U.S. Appl. No. 14/825,669, Non Final Office Action dated Jun. 23, 2017", 9 pgs.
"U.S. Appl. No. 14/825,669, Response filed Jun. 8, 2017 to Final Office Action dated Mar. 9, 2017", 14 pgs.
"U.S. Appl. No. 15/082,440, Corrected Notice of Allowance dated Feb. 9, 2018", 5 pgs.
"U.S. Appl. No. 15/082,440, Examiner Interview Summary dated Sep. 6, 2017", 2 pgs.
"U.S. Appl. No. 15/082,440, Non Final Office Action dated Jun. 21, 2017", 9 pgs.
"U.S. Appl. No. 15/082,440, Notice of Allowance dated Jan. 18, 2018", 8 pgs.
"U.S. Appl. No. 15/082,440, Notice of Allowance dated Sep. 25, 2017", 10 pgs.
"U.S. Appl. No. 15/082,440, Response filed May 17, 2017 to Restriction Requirement dated Mar. 30, 2017", 9 pgs.
"U.S. Appl. No. 15/082,440, Response filed Sep. 5, 2017 to Non Final Office Action dated Jun. 21, 2017", 14 pgs.
"U.S. Appl. No. 15/082,440, Restriction Requirement dated Mar. 30, 2017", 7 pgs.
"U.S. Appl. No. 15/967,326, Advisory Action dated Mar. 14, 2019", 3 pgs.
"U.S. Appl. No. 15/967,326, Final Office Action dated Jan. 3, 2019", 11 pgs.
"U.S. Appl. No. 15/967,326, Non Final Office Action dated Apr. 18, 2019", 9 pgs.
"U.S. Appl. No. 15/967,326, Non Final Office Action dated Jun. 29, 2018", 9 pgs.
"U.S. Appl. No. 15/967,326, Response filed Feb. 21, 2019 to Final Office Action dated Jan. 3, 2019", 11 pgs.
"U.S. Appl. No. 15/967,326, Response filed Sep. 24, 2018 to Non Final Office Action dated Jun. 29, 2018", 13 pgs.
"Australian Application Serial No. 2015301633, First Examiners Report dated Sep. 7, 2017", 3 pgs.
"Australian Application Serial No. 2015301633, Response filed Mar. 21, 2018 to First Examiners Report dated Sep. 7, 2017", 14 pgs.
"Chinese Application Serial No. 201580047246.7, Office Action dated Mar. 6, 2019", w/ English Translation, 19 pgs.
"European Application Serial No. 15757059.9, Response filed Sep. 26, 2017 to Communication Pursuant to Rules 161(1) and 162 EPC dated Mar. 21, 2017", 18 pgs.
"European Application Serial No. 16715709.8, Response filed Jun. 27, 2018 to Communication Pursuant to Rules 161(1) and 162 EPC dated Dec. 7, 2017", 28 pgs.
"International Application Serial No. PCT/US2015/045042, International Preliminary Report on Patentability dated Feb. 23, 2017", 10 pgs.
"International Application Serial No. PCT/US2016/024463, International Preliminary Report on Patentability dated Oct. 12, 2017", 8 pgs.
"International Application Serial No. PCT/US2016/060050, International Preliminary Report on Patentability dated May 17, 2018", 7 pgs.
"International Application Serial No. PCT/US2016/060050, International Search Report dated Feb. 6, 2017", 4 pgs.
"International Application Serial No. PCT/US2016/060050, Written Opinion dated Feb. 6, 2017", 5 pgs.
"Japanese Application Serial No. 2017-508064, Office Action dated Mar. 6, 2018", With English Translation, 4 pgs.
"Japanese Application Serial No. 2017-508064, Response filed May 30, 2018 to Office Action dated Mar. 6, 2018", w/ English claims, 10 pgs.
"Japanese Application Serial No. 2017-550731, Notification of Reasons for Refusal dated Dec. 18, 2018", w/ English summary, 6 pgs.
"Japanese Application Serial No. 2017-550731, Office Action dated Sep. 4, 2018", w/ English translation (machine), 8 pgs.

(56) References Cited

OTHER PUBLICATIONS

"Japanese Application Serial No. 2017-550731, Response filed Mar. 15, 2019 to Notification of Reasons for Refusal dated Dec. 18, 2018", w/ English claims, 6 pgs.

"Japanese Application Serial No. 2017-550731, Response filed Nov. 28, 2018 to Office Action dated Sep. 4, 2018", w/ English claims, 8 pgs.

Pürerfellner, H., et al., "P-wave evidence as a method for improving algorithm to detect atrial fibrillation in insertable cardiac monitors", Heart Rhythm; vol. 11, Issue 9, (Sep. 2014), 1575-1583.

"International Application Serial No. PCT/US2015/045042, International Search Report dated Oct. 27, 2015", 6 pgs.

"International Application Serial No. PCT/US2015/045042, Written Opinion dated Oct. 27, 2015", 9 pgs.

"International Application Serial No. PCT/US20161024463, International Search Report dated Jun. 17, 2016", 6 pgs.

"International Application Serial No. PCT/US2016/024463, Written Opinion dated Jun. 17, 2016", 6 pgs.

Babaeizadeh, Saeed, et al., "Improvements in atrial fibrillation detection for real-time monitoring", Journal of Electrocardiology, Elsevier Science vol. 42, No. 6,, (Nov. 1, 2009), 522-526.

Esperer, et al., "Cardiac arrhythrnias imprint specific signatures on Lorenz plots", Ann Noninvasive Electrocardiol, (2008), 44-60 pgs.

Tateno, K, et al., "Automatic detection of atrial fibrillation using the coefficient of variation and density histograms of RR and RR intervals", Medical and Biological Engineering and Computing, vol. 39, No. 6,, (Nov. 1, 2011), 664-671.

METHOD AND APPARATUS FOR ENHANCING VENTRICULAR BASED ATRIAL FIBRILLATION DETECTION USING ATRIAL ACTIVITY

CLAIM OF PRIORITY

This application claims the benefit of priority under 35 U.S.C. § 119(e) of U.S. Provisional Patent Application Ser. No. 62/252,014, filed on Nov. 6, 2015, which is herein incorporated by reference in its entirety atrial activity.

TECHNICAL FIELD

This document relates generally to cardiac rhythm management and more particularly to method and apparatus for enhancing ventricular interval-based detection of atrial fibrillation (AF) by analyzing atrial activity.

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to cause the muscular tissues of these regions to depolarize and contract at a normal sinus rate.

Tachyarrhythmia occurs when the heart contracts at a rate higher than the normal sinus rate. Tachyarrhythmia generally includes ventricular tachyarrhythmia (VT) and supraventricular tachyarrhythmia (SVT). VT occurs, for example, when a pathological conduction loop formed in the ventricles through which electrical impulses travel circularly within the ventricles, or when a pathologically formed electrical focus generates electrical impulses from the ventricles. SVT can be physiologic (e.g., sinus tachycardia) or pathologic (e.g., atrial fibrillation). The physiologic sinus tachycardia occurs when the SA node generates the electrical impulses at a particularly high rate. A pathologic SVT occurs, for example, when a pathologic conduction loop forms in an atrium or both atria. Fibrillation occurs when the heart contracts at a tachyarrhythmic rate with an irregular rhythm. Ventricular fibrillation (VF), as a ventricular arrhythmia with an irregular conduction, is a life threatening condition requiring immediate medical treatment such as ventricular defibrillation. Atrial fibrillation (AF), as an SVT with an irregular rhythm, though not directly life threatening, also needs medical attention for purposes such as assessing a patient's cardiovascular conditions, atrial defibrillation, and/or adjusting other therapies received by the patient to restore cardiovascular functions and/or to prevent the deterioration of the heart.

SUMMARY

An example (e.g., "Example 1") of a system may include a sensing circuit and an atrial fibrillation (AF) detection circuit. The sensing circuit may be configured to sense a cardiac signal indicative of atrial and ventricular depolarizations. The AF detection circuit may be configured to detect AF using the cardiac signal, and may include a detector and a detection enhancer. The detector may be configured to detect the ventricular depolarizations using the cardiac signal, to measure ventricular intervals each between two successively detected ventricular depolarizations, and to detect AF using the ventricular intervals. The detection enhancer may be configured to generate atrial detection windows each being a time interval prior to each of the detected ventricular depolarizations, to compute an atrial activity score using a rolling average of portions of the cardiac signal within the atrial detection windows, and to verify the detection of the AF using the atrial activity score and an atrial activity threshold. The atrial activity score is a measure of consistency between a relationship between the atrial depolarizations and the ventricular depolarizations.

In Example 2, the subject matter of Example 1 may optionally be configured such that the detector is configured to compute a measure of ventricular rate variability using the ventricular intervals and to indicate a suggested detection of AF in response the measure of ventricular rate variability satisfying one or more criteria for AF.

In Example 3, the subject matter of any one or any combination of Examples 1 and 2 may optionally be configured such that the detection enhancer is configured to compute the rolling average by filtering the portions of the atrial signal within the atrial detection window using an infinite impulse response (IIR) low-pass filter, to compute the atrial activity score using the portions of the atrial signal filtered for a specified number of the detected ventricular depolarizations, to compare the atrial activity score to the atrial activity threshold, and to indicate a verified detection of AF using an outcome of the comparison.

In Example 4, the subject matter of Example 3 may optionally be configured such that the detection enhancer is configured to generate the atrial detection windows each starting at about 160 to 400 milliseconds before the each of the detected ventricular depolarizations and ending at about 40 to 100 milliseconds before the each of the detected ventricular depolarizations.

In Example 5, the subject matter of any one or any combination of Examples 3 and 4 may optionally be configured such that the detection enhancer is configured to create a vector $V_i$ of a length N, N being a number of samples in each of the atrial detection windows, to initialize all elements of $V_i$, to update each vector value $V_i$ for the each of the detected ventricular depolarizations using a value of sample $S_i$ of the portion of the atrial signal within the each of the atrial detection windows, to compute the atrial activity score y after M R-waves, M related to an aggression parameter of the IIR low-pass filter and being large enough for $V_i$ to saturate, and to indicate the verified detection of AF in response to y being less than the atrial activity threshold.

In Example 6, the subject matter of Example 5 may optionally be configured such that the detection enhancer is configured to update each vector value $V_i$ for the each of the detected ventricular depolarizations using:

$$V_i = \alpha V_i + (1-\alpha) S_i,$$

where $\alpha$ is the aggression parameter of the IIR low-pass filter.

In Example 7, the subject matter of Example 6 may optionally be configured such that the detection enhancer is configured to compute the atrial activity score using:

$$y = \sum_N |V_i - Q_i|,$$

where $Q_i$ is a function numerically fitted to $V_i$ to compensate for short-term baseline fluctuation in the cardiac signal.

In Example 8, the subject matter of any one or any combination of Examples 1 to 7 may optionally be configured to include an implantable medical device including the sensing circuit and the AF detection circuit.

In Example 9, the subject matter of Example 8 may optionally be configured such that the sensing circuit is configured to sense a ventricular electrogram.

In Example 10, the subject matter of Example 8 may optionally be configured such that the sensing circuit is configured to sense a subcutaneous electrocardiogram.

In Example 11, the subject matter of Example 8 may optionally be configured such that the implantable medical device includes an implantable loop recorder.

In Example 12, the subject matter of any one or any combination of Examples 1 to 11 may optionally be configured to further include a therapy device and a therapy control circuit. The therapy device may be configured to deliver one or more therapies. The therapy control circuit may be configured to control the delivery of the one or more therapies based on whether the detection of the AF is verified.

In Example 13, the subject matter of Example 12 may optionally be configured such that the implantable medical device includes a subcutaneous implantable cardioverter defibrillator.

In Example 14, the subject matter of Example 12 may optionally be configured such that the implantable medical device includes a ventricular implantable cardioverter defibrillator.

In Example 15, the subject matter of any one or any combination of Examples 1 to 14 may optionally be configured to further include a storage device and a storage control circuit. The storage device may be configured to store the sensed cardiac signal. The storage control circuit may be configured to start storage of the sensed cardiac signal in response to the detection of the AF being verified.

An example (e.g., "Example 16") of a method is also provided, the method may include sensing a cardiac signal indicative of atrial and ventricular depolarizations; detecting the ventricular depolarizations using the cardiac signal; measuring ventricular intervals each between two successively detected ventricular depolarizations; detecting atrial fibrillation (AF) using the ventricular intervals; generating atrial detection windows each being a time interval prior to each of the detected ventricular depolarizations; computing an atrial activity score using a rolling average of portions of the cardiac signal within the atrial detection windows, the atrial activity score being a measure of consistency between a relationship between the atrial depolarizations and the ventricular depolarizations; and verifying the detection of the AF using the atrial activity score and an atrial activity threshold.

In Example 17, the subject matter of detecting the AF using the ventricular intervals as found in Example 16 may optionally include computing a measure of ventricular rate variability using the ventricular intervals and indicating a suggested detection of AF in response to the measure of ventricular rate variability satisfying one or more criteria for AF.

In Example 18, the subject matter of computing the atrial activity score as found in any one or any combination of Examples 16 and 17 may optionally include filtering the portions of the atrial signal within the atrial detection window using an infinite impulse response (IIR) low-pass filter, and computing the atrial activity score using the portions of the atrial signal filtered for a specified number of the detected ventricular depolarizations.

In Example 19, the subject matter of generating the atrial detection windows as found in any one or any combination of Examples 16 to 18 may optionally include generating the atrial detection windows each starting at about 160 to 400 milliseconds before the each of the detected ventricular depolarizations and ending at about 40 to 100 milliseconds before the each of the detected ventricular depolarizations.

In Example 20, the subject matter of filtering the portions of the atrial signal within the atrial detection window using an IIR low-pass filter as found in any one or any combination of Examples 18 and 19 may optionally include creating a vector $V_i$ of a length N, N being a number of samples in each of the atrial detection windows; initializing all elements of $V_i$; and updating each vector value $V_i$ for the each of the detected ventricular depolarizations using a value of sample $S_i$ of the portion of the atrial signal within the each of the atrial detection windows.

In Example 21, the subject matter of updating the each vector value $V_i$ for the each of the detected ventricular depolarizations as found in Example 20 may optionally include updating the each vector value $V_i$ for the each of the detected ventricular depolarizations using:

$$V_i = \alpha V_i + (1-\alpha) S_i,$$

where $\alpha$ is the aggression parameter of the IIR low-pass filter.

In Example 22, the subject matter of computing the atrial activity score as found in any one or any combination of Examples 20 and 21 may optionally include computing the atrial activity score y after M R-waves, M related to an aggression parameter of the IIR low-pass filter and being large enough for $V_i$ to saturate.

In Example 23, the subject matter of computing the atrial activity score as found in Example 22 may optionally include computing the atrial activity score using:

$$y = \sum_N |V_i - Q_i|,$$

where $Q_i$ is a function numerically fitted to $V_i$ to compensate for short-term baseline fluctuation in the cardiac signal.

In Example 24, the subject matter of verifying the detection of the AF as found in any one or any combination of Examples 22 and 23 may optionally further include indicating a verified detection of AF in response to y being less than the atrial activity threshold.

In Example 25, the subject matter any one or any combination of Examples 16 to 24 may optionally further include triggering a storage of the sensed cardiac signal in response to the detection of the AF being verified.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
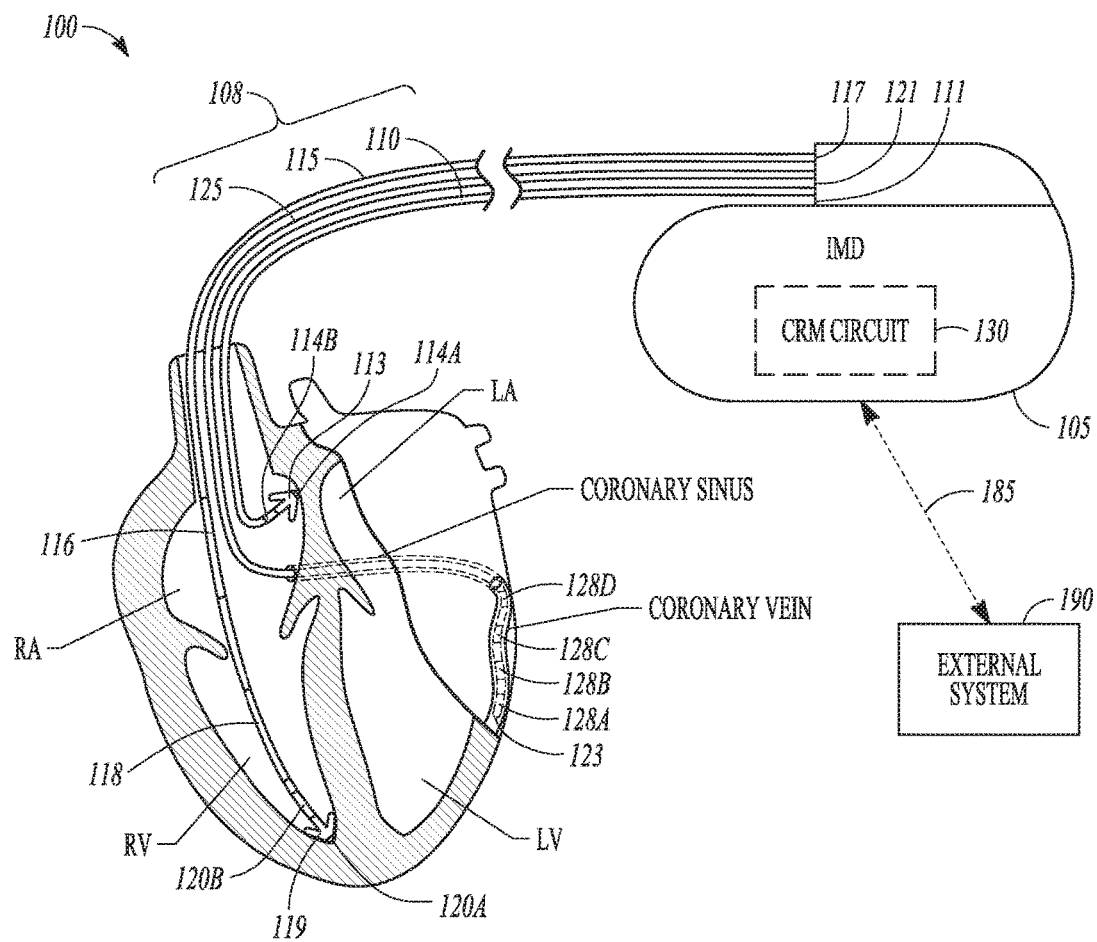
FIG. 1 is an illustration of an embodiment of a cardiac rhythm management (CRM) system and portions of an environment in which the CRM system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a method and system for detecting atrial fibrillation (AF, also referred to as "AFib"). Existing methods for detecting AF include algorithms based on ventricular rate variability (or ventricular cycle length variability, also referred to as R-R variability or V-V variability), which is a measure of the beat-to-beat variance in ventricular intervals (time interval between two successive ventricular depolarizations, or R-waves). Such methods, however, may give false-positives sometimes due to variations in the ventricular rate not resulting from variations in the atrial rate. The present system detects AF using ventricular intervals and verifies the detection of the AF using available atrial information. When the AF is detected based on a certain number of ventricular depolarizations, atrial activity is analyzed to determine whether an atrial depolarization consistently precedes each ventricular depolarization for the certain number of ventricular depolarizations. The detection of AF is verified by lacking of such consistency.

In various embodiments, the AF detection and verification are performed for diagnostic and/or therapeutic purposes. In an embodiment, a verified AF detection may trigger storage of a cardiac signal for monitoring and diagnosing of arrhythmic conditions in a patient, and the storage may continue until AF is no longer detected or verified. In another embodiment, delivery of a therapy to a patient may be started, stopped, or adjusted in response to a verified AF detection. While some specific devices are discussed in this document as examples, the present system and method may be employed in any device and system where AF is to be detected.

The relationship between a heart rate and a cardiac interval (also known as cardiac cycle length), as used in this document, is the relationship between a frequency and its corresponding period. If a heart rate is given in beats per minute (bpm), its corresponding cardiac interval in milliseconds is calculated by dividing 60,000 by the heart rate (where 60,000 is the number of milliseconds in a minute). Any process, such as a comparison, using a heart rate is to be modified accordingly when a cardiac interval is used instead. Examples of the heart rate include atrial rate and ventricular rate. Examples of the cardiac interval (or cycle length) include atrial interval (or cycle length) and ventricular interval (or cycle length).

In this document, "user" includes a physician or other caregiver who examines and/or treats a patient using one or more of the methods and apparatuses reported in the present document.

FIG. 1 is an illustration of an embodiment of a cardiac rhythm management (CRM) system 100 and portions of an environment in which system 100 operates. CRM system 100 includes an implantable medical device (IMD) 105 that is electrically coupled to a patient's heart through a lead system 108 including implantable leads 110, 115, and 125. An external system 190 communicates with IMD 105 via a telemetry link 185. CRM system 100 is discussed as only an example in which AF may be detected. In various embodiments, the present system and method may be implemented in any implantable or non-implantable devices where AF needs to be detected and one or more signals indicative of atrial and ventricular depolarization are available. For example, while the illustrated embodiment includes cardiac pacing and cardioversion/defibrillation, various embodiments may allow AF to be detected for monitoring only or for controlling various types of therapies. While the illustrated embodiment allows for sensing of multiple intracardiac atrial and ventricular electrograms, various embodiments may allow AF to be detected using one or more cardiac signals of any type that indicates atrial and ventricular depolarizations.

IMD 105 includes a hermetically sealed can housing an electronic circuit that senses physiological signals and delivers therapeutic electrical pulses. The hermetically sealed can also functions as an electrode (referred to as "the can electrode" hereinafter) for sensing and/or pulse delivery purposes. IMD 105 senses one or more cardiac signals indicative of cardiac electrical events, including depolarization and repolarization in each of the chambers (RA, RV, LA, and LV), and generates cardiac data representative of the one or more cardiac signals. In one embodiment, IMD 105 includes a pacemaker that delivers cardiac pacing therapies. In another embodiment, IMD 105 includes the pacemaker and a cardioverter/defibrillator that delivers cardioversion/defibrillation therapies. In various embodiments, IMD 105 includes one or more devices selected from monitoring devices and therapeutic devices such as the pacemaker, the cardioverter/defibrillator, a neurostimulator, a drug delivery device, and a biological therapy device.

IMD 105 includes a CRM circuit 130 that performs AF detection and verification according to the present subject matter. In various embodiments, the AF detection and verification may be performed for monitoring and diagnostic purposes, and/or for controlling one or more therapies delivered by IMD 105. An embodiment of CRM circuit 130 is discussed below with reference to FIG. 2.

Lead 110 is an RA pacing lead that includes an elongate lead body having a proximal end 111 and a distal end 113. Proximal end 111 is coupled to a connector for connecting to IMD 105. Distal end 113 is configured for placement in the RA in or near the atrial septum. Lead 110 includes an RA tip electrode 114A, and an RA ring electrode 114B. RA electrodes 114A and 114B are incorporated into the lead body at distal end 113 for placement in or near the atrial septum, and are each electrically coupled to IMD 105 through a conductor extending within the lead body. RA tip electrode 114A, RA ring electrode 114B, and/or the can electrode allow for sensing an RA electrogram indicative of RA depolarizations (P-waves) and delivering RA pacing pulses.

Lead 115 is an RV pacing-defibrillation lead that includes an elongate lead body having a proximal end 117 and a distal end 119. Proximal end 117 is coupled to a connector for connecting to IMD 105. Distal end 119 is configured for placement in the RV. Lead 115 includes a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA and/or the superior vena cava (SVC). Defibrillation electrode 118 is incorporated into the lead body near distal end 119 for placement in the RV. RV electrodes 120A and 120B are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or the can electrode allow for delivery of cardioversion/defibrillation pulses to the heart. RV tip electrode 120A, RV ring electrode 120B, and/or the can of IMD 105 allow for sensing an RV electrogram indicative of RV depolarizations (R-waves) and delivering RV pacing pulses. In various embodiments, proximal defibrillation electrode 116 and/or distal defibrillation electrode 118 may also be used for sensing the RV electrogram.

Lead 125 is an LV coronary pacing lead that includes an elongate lead body having a proximal end 121 and a distal end 123. Proximal end 121 is coupled to a connector for connecting to IMD 105. Distal end 123 is configured for placement in the coronary vein. Lead 125 includes a plurality of LV electrodes 128A-D. In the illustration embodiment, the distal portion of lead 125 is configured for placement in the coronary vein such that LV electrodes 128A-D are placed in the coronary vein. In another embodiment, the distal portion of lead 125 can be configured for placement in the coronary sinus and coronary vein such that LV electrodes 128A-D are placed in the coronary sinus and coronary vein. In various embodiments, lead 125 can be configured for LV electrodes 128A-D to be placed in various locations in or on the LV for desirable pattern of LV excitation using pacing pulses. LV electrodes 128A-D are each incorporated into the distal portion of lead 125 and are each electrically coupled to IMD 105 through a conductor extending within the lead body. LV electrode 128A, LV electrode 128B, LV electrode 128C, LV electrode 128D, and/or the can electrode allow for sensing an LV electrogram indicative of LV depolarizations (R-Wave) and delivering LV pacing pulses.

Electrodes from different leads may also be used to sense an electrogram or deliver pacing or cardioversion/defibrillation pulses. For example, an electrogram may be sensed using an electrode selected from RV electrode 116, 118, and 120A-B and another electrode selected from LV electrode 128A-D. The lead configuration including RA lead 110, RV lead 115, and LV lead 125 is illustrated in FIG. 1 by way of example and not by way of restriction. Other lead configurations may be used, depending on monitoring and therapeutic requirements. For example, lead 115 may not include defibrillation electrodes 116 and 118 when capability of delivering cardioversion/defibrillation therapy is not needed, additional leads may be used to provide access to additional cardiac regions, and leads 110, 115, and 125 may each include more or fewer electrodes along the lead body at, near, and/or distant from the distal end, depending on specified monitoring and therapeutic needs. In various embodiments, IMD 105 is programmable for sensing the one or more cardiac signals and delivering pacing pulses using any combination of electrodes, such as those illustrated in FIG. 1, to accommodate various pacing configurations as discussed in this document.

External system 190 allows for programming of IMD 105 and receives signals acquired by IMD 105. In one embodiment, external system 190 includes a programmer. In another embodiment, external system 190 includes a patient monitoring system such as the system discussed below with reference to FIG. 3. In one embodiment, telemetry link 185 is an inductive telemetry link. In an alternative embodiment, telemetry link 185 is a far-field radio-frequency telemetry link. Telemetry link 185 provides for data transmission from IMD 105 to external system 190. This may include, for example, transmitting real-time physiological data acquired by IMD 105, extracting physiological data acquired by and stored in IMD 105 (such as a cardiac signal recorded and stored during an AF or other arrhythmia episode), extracting therapy history data stored in IMD 105, and extracting data indicating an operational status of IMD 105 (e.g., battery status and lead impedance). The physiological data include the cardiac data representative of the one or more cardiac signals. Telemetry link 185 also provides for data transmission from external system 190 to IMD 105. This may include, for example, programming IMD 105 to acquire physiological data, programming IMD 105 to perform at least one self-diagnostic test (such as for a device operational status), programming IMD 105 to run a signal analysis algorithm (such as an algorithm implementing the AF detection and verification method discussed in this document), and programming IMD 105 to deliver pacing and/or cardioversion/defibrillation therapies.

Figure 2:
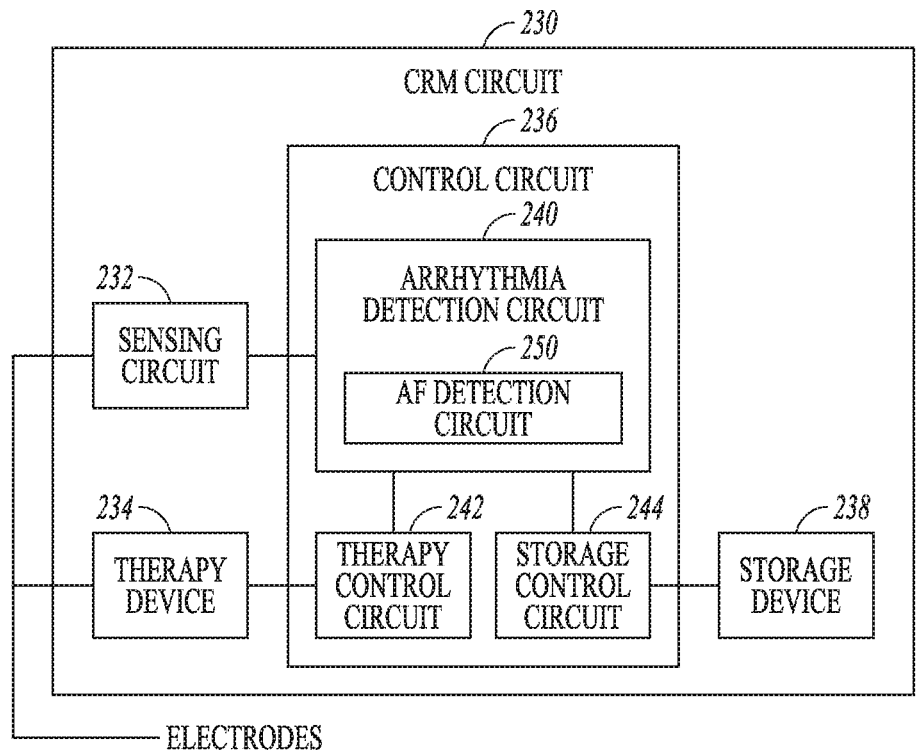
FIG. 2 is a block diagram illustrating an embodiment of a CRM circuit, such as the CRM circuit of the CRM system of FIG. 1.

FIG. 2 is a block diagram illustrating an embodiment of a CRM circuit 230. In one embodiment, CRM circuit is configured for use as CRM circuit 130, i.e., for use in an implantable device such as IMD 105. In various other embodiments, CRM circuit 230 can be configured for use in any medical device that detects AF, with examples further discussed below with reference to FIG. 8. CRM circuit 230 can include a sensing circuit 232, a therapy device 234, a control circuit 236, and a storage device 238.

Sensing circuit 232 senses one or more cardiac signals indicative of atrial depolarizations (P-waves) and ventricular depolarizations (R-waves). Examples of such one or more cardiac signals include one or more electrocardiograms (ECGs), one or more subcutaneous ECGs, and one or more intracardiac electrograms (such as atrial and ventricular electrograms).

Therapy device 234 delivers one or more therapies. Examples of such one or more therapies include a cardiac pacing circuit to deliver cardiac pacing pulses, a cardioversion/defibrillation circuit to deliver cardioversion/defibrillation shocks, a neurostimulation circuit to deliver neurostimulation pulses or other form of neurostimulation energy, a drug delivery device to deliver one or more drugs, and a biologic therapy device to deliver one or more biologic therapies. In various embodiments, the one or more therapies are each for treatment of AF and/or necessarily or preferably adjusted based on whether AF is detected.

Storage device 238 stores portions of the sensed one or more cardiac signals. In various embodiments, storage device 238 also stores various control algorithms used by control circuit 236 as well as other signals acquired by CRM circuit 230.

Control circuit 236 controls the operation of CRM circuit 230 and can include an arrhythmia detection circuit 240, a therapy control circuit 242, and a storage control circuit 244. Arrhythmia detection circuit 240 detects one or more types of cardiac arrhythmias using the one or more cardiac signals, and includes an AF detection circuit 250 to detect AF using the one or more cardiac signals. An embodiment of AF detection circuit 250 is discussed below with reference to FIG. 3. Therapy control circuit 242 controls the delivery of the one or more therapies from therapy device 234 using the one or more cardiac signals. In various embodiments, therapy control circuit 242 starts, stops, or adjusts the delivery of a therapy of the one or more therapies in response to a detection of a type of arrhythmia of the one or more types of cardiac arrhythmias. In various embodiments, therapy control circuit 242 controls the delivery of the one or more therapies based on whether AF is detected and verified, and can be configured to start, stop, or adjust the delivery of a therapy of the one or more therapies in response to a verified detection of AF. Storage control circuit 238 starts storage of the one or more cardiac signals in response to a detection of a type of arrhythmia of the one or more types of cardiac arrhythmias. In one embodiment, storage control circuit 238 stops the storage of the one or more cardiac signals when the type of arrhythmia is no longer detected. In various embodiments, storage control circuit 238 starts storage of the one or more cardiac signals in response to a verified detection of AF, and stops the storage when the AF is no longer detected or verified.

Figure 3:
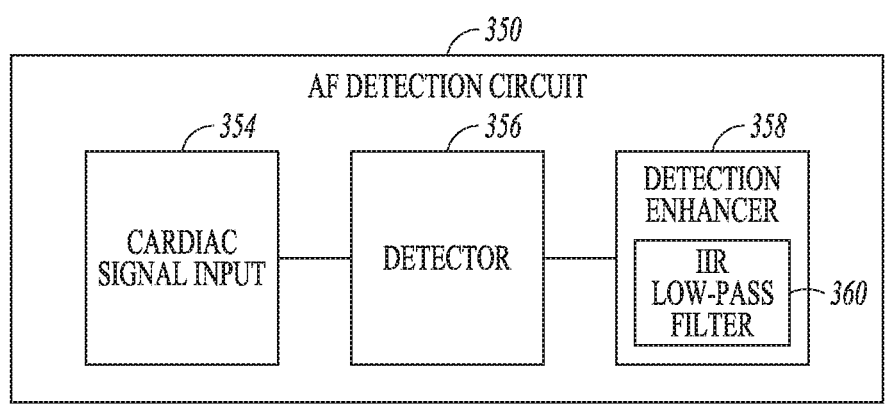
FIG. 3 is a block diagram illustrating an embodiment of an atrial fibrillation (AF) detection circuit.

FIG. 3 is a block diagram illustrating an embodiment of an AF detection circuit 350. AF detection circuit 350 represents an embodiment of AF detection 250 and can include a cardiac signal input, a detector 356, and a detection enhancer 358. AF detection circuit 350 detects AF using a cardiac signal indicative of atrial and ventricular depolarizations.

Cardiac signal input 354 receives the cardiac signal indicative of atrial and ventricular depolarizations. In various embodiments, the cardiac signal may include a single signal indicative of both atrial and ventricular depolarizations or multiple signals each indicative of at least one of the atrial depolarizations and ventricular depolarizations. Examples of the cardiac signal include the one or more cardiac signal sensed by sensing circuit 232.

Detector 356 can be configured to detect the ventricular depolarizations (R-waves) using the cardiac signal, to measure ventricular intervals (R-R intervals) each between two successively detected ventricular depolarizations, and to detect AF using the ventricular intervals. In one embodiment, detector 356 computes a measure of ventricular rate variability using the ventricular intervals, and indicates a suggested detection of AF in response the measure of ventricular rate variability satisfying one or more criteria for AF. The ventricular rate variability (or ventricular cycle length variability, also referred to as the R-R variability or V-V variability) corresponds to heart rate variability (HRV) measured over a relatively short period. In one embodiment, detector 356 measures the ventricular intervals each associated with a detected ventricular depolarization, and determines the ventricular rate variability as the beat-to-beat variance in the ventricular intervals over a specified number of heart beats or over a specified time interval. Examples of AF detection using ventricular rate variability are discussed in U.S. patent application Ser. No. 14/825,669, entitled "ATRIAL FIBRILLATION DETECTION USING VENTRICULAR RATE VARIABILITY", filed on Aug. 13, 2015, and U.S. Provisional Patent Application Ser. No. 62/142,184, entitled "ATRIAL FIBRILLATION DETECTION", filed on Apr. 2, 2015, both assigned to Cardiac Pacemakers, Inc., which are incorporated herein by reference in their entirety.

Detection enhancer 358 can be configured to generate atrial detection windows each being a time interval prior to each of the detected ventricular depolarizations, to compute an atrial activity score using a rolling average of portions of the cardiac signal within the atrial detection windows, and to verify the detection of the AF using the atrial activity score and an atrial activity threshold. The atrial activity score is a measure of consistency between a relationship between the atrial depolarizations and the ventricular depolarizations. In one embodiment, detection enhancer 358 includes an HR low-pass filter 360 and computes the rolling average of the portions of the atrial signal by filtering the atrial signal during the atrial detection windows using an IIR low-pass filter. Then, detection enhancer 358 computes the atrial activity score using the atrial signal filtered for a specified number of detected ventricular depolarizations, compares the atrial activity score to the atrial activity threshold, and indicates a verified detection of AF using an outcome of the comparison. The verified detection of AF indicates that the suggested detection of AF as indicated by detector 356 is now verified.

Figure 4:
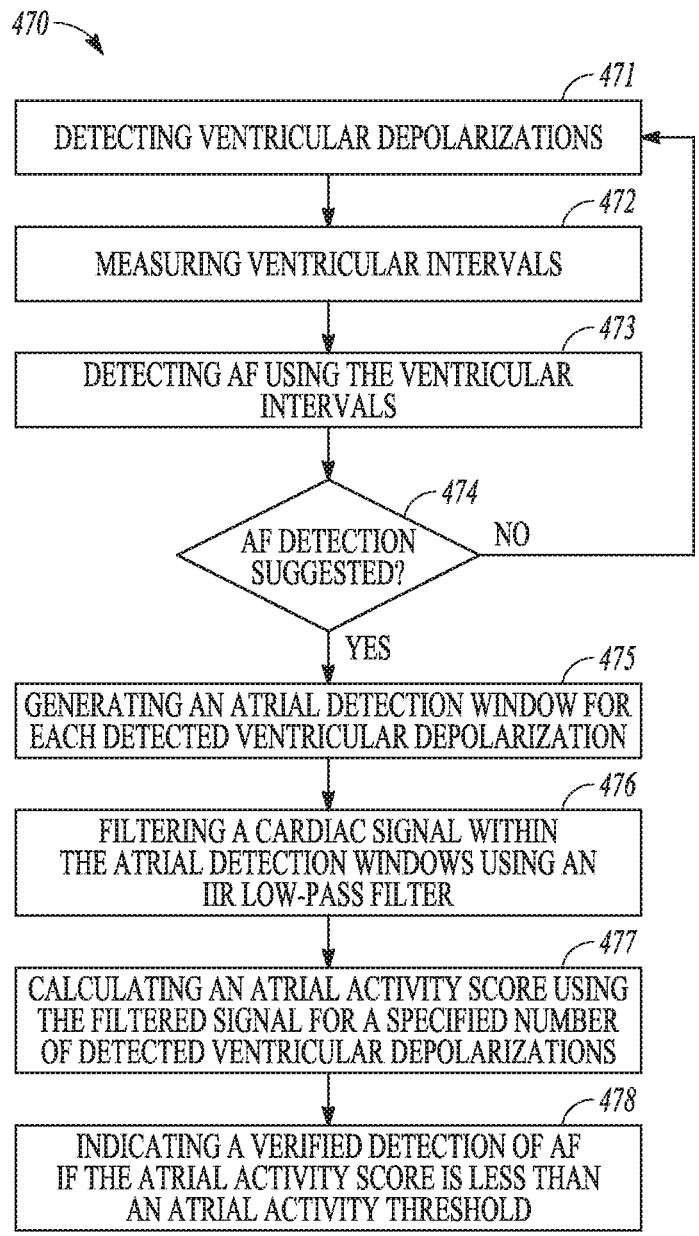
FIG. 4 is a flow chart illustrating an embodiment of a method for detecting AF.

FIG. 4 is a flow chart illustrating an embodiment of a method 470 for detecting AF. In one embodiment, AF detection circuit 350 is configured to perform method 470. For example, detector 356 can be configured to perform steps 471-473, and detection enhancer 358 can be configured to perform steps 474-478.

At 471, ventricular depolarizations are detected from a cardiac signal. Examples of the cardiac signal include the one or more cardiac signal sensed by sensing circuit 232. At 472, ventricular intervals are measured. At 473, AF is detected using the ventricular intervals. In various embodiments, a parameter representative of ventricular rate variability is computed using the ventricular intervals, and AF is detected based on that parameter.

At 475, an atrial detection window is generated for each detected ventricular depolarization, if at 474, a suggested detection of AF is indicated as a result of step 473. The atrial detection window is a time interval prior to each detected ventricular depolarization during which an atrial depolarization is to be detected. In various embodiments, the atrial detection window is set to start at about 160 to 400 milliseconds before each detected ventricular depolarization and to end at about 40 to 100 milliseconds before each detected ventricular depolarization. In one embodiment, the rate at which the cardiac signal is sampled is 200 Hz, and the atrial detection window is set to be 40 samples wide, starting at 250 milliseconds before each detected ventricular depolarization and end at 50 milliseconds before each detected ventricular depolarization.

Figure 5:
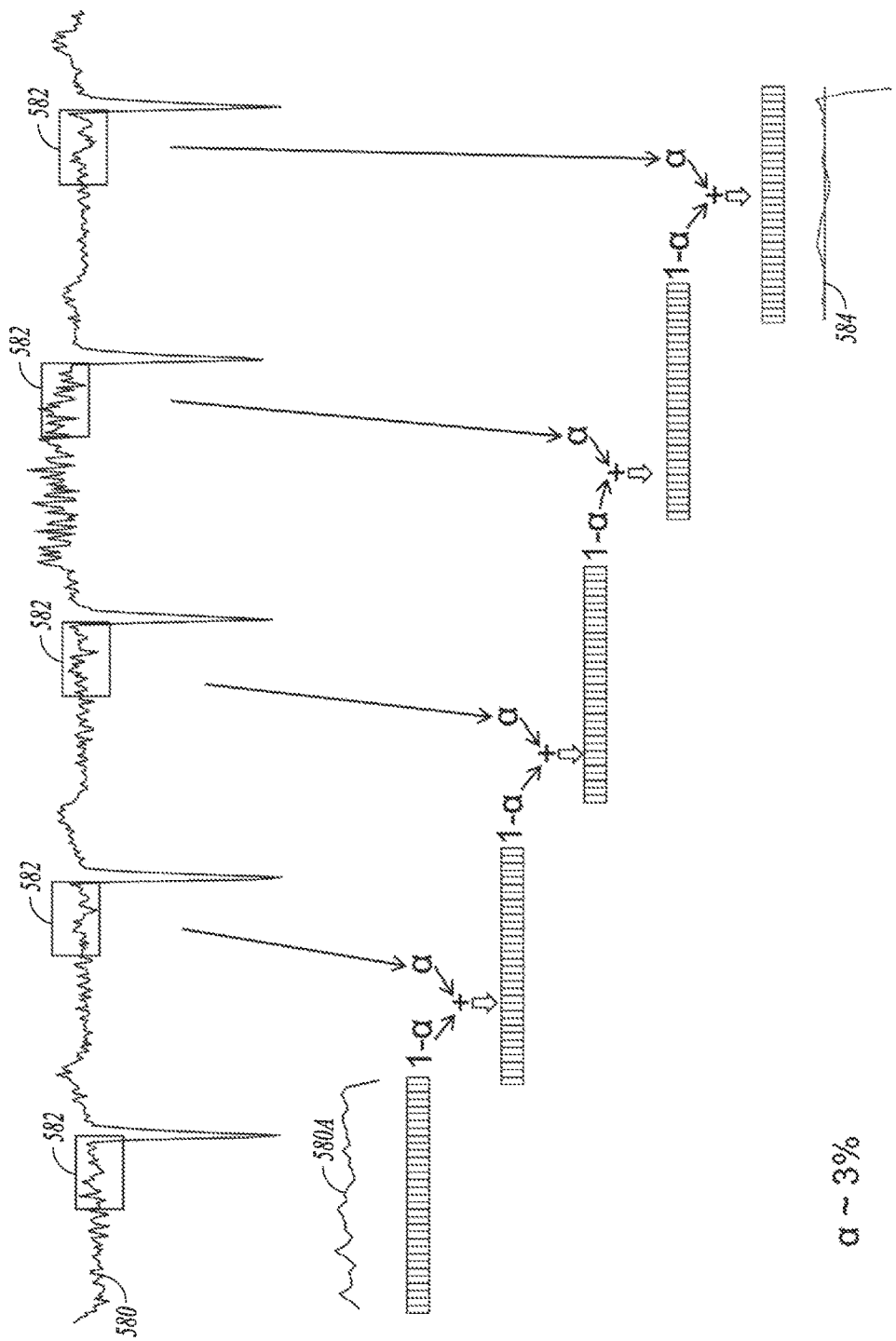
FIG. 5 is an illustration of an example of a vector resulting from filtering a cardiac signal during atrial detection windows using an infinite impulse response (IIR) low-pass filter.

At 476, the cardiac signal is filtered within the atrial detection windows using an IIR low-pass filter. This includes creating a vector $V_i$ of length N, where N is the number of samples in the atrial detection window. All the elements of $V_i$ are initialized to zero or to the data from the first atrial detection window (the atrial detection window prior to the first detected ventricular depolarization). In response to each detection of the ventricular depolarization, each vector value $V_i$ is updated by replacing it with a combination of its value and the value of a sample $S_i$ of the filtered cardiac signal, using equation [1]:

$$V_i = \alpha V_i + (1-\alpha) S_i \quad [1]$$

where α is the aggression parameter of the IIR low-pass filter, a number between 0 and 1 (e.g., 0.03). FIG. 5 is an illustration of an example of vector $V_i$ resulting from filtering a cardiac signal 580 during atrial detection windows 582 using the IIR low-pass filter. As illustrated in FIG. 5, signal 580A is a portion of cardiac signal 580 that is within one of the atrial detection windows 582, and signal 584 is the filtered cardiac signal.

At 476, an atrial activity score y is calculated after M detected ventricular depolarizations, where M is related to α and large enough for V to saturate (e.g., 2/α), using equation [2]:

$$y = \sum_N |V_i - Q_i|, \quad [2]$$

where $Q_i$ is a function numerically fitted to $V_i$ to compensate for short-term baseline fluctuation in the cardiac signal when such compensation is needed. In one embodiment, $Q_i$ is a quadratic fitted to $V_i$.

Figure 6:
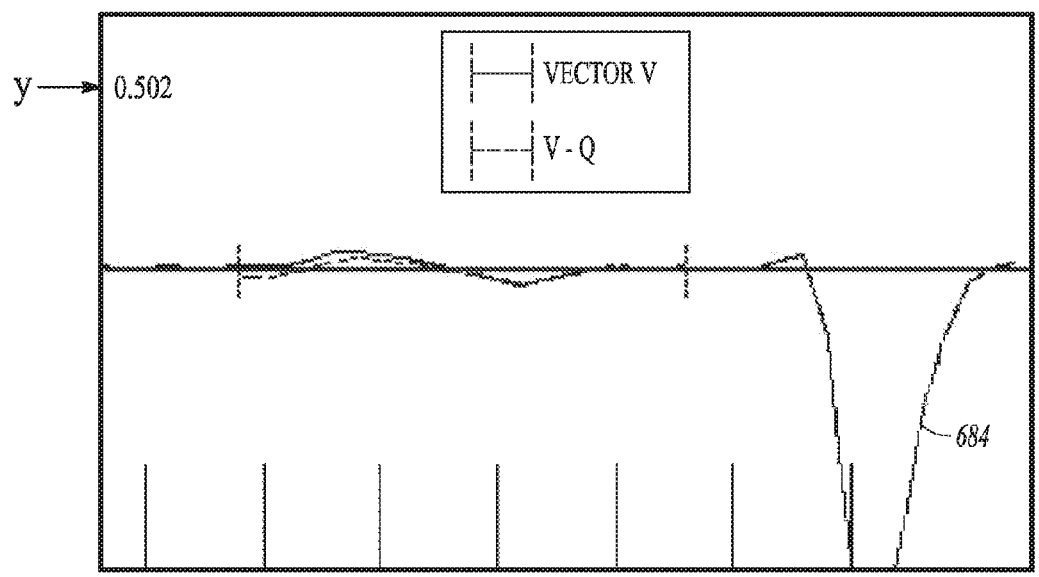
FIG. 6 is an illustration of an example of the vector indicating a normal sinus rhythm.
Figure 7:
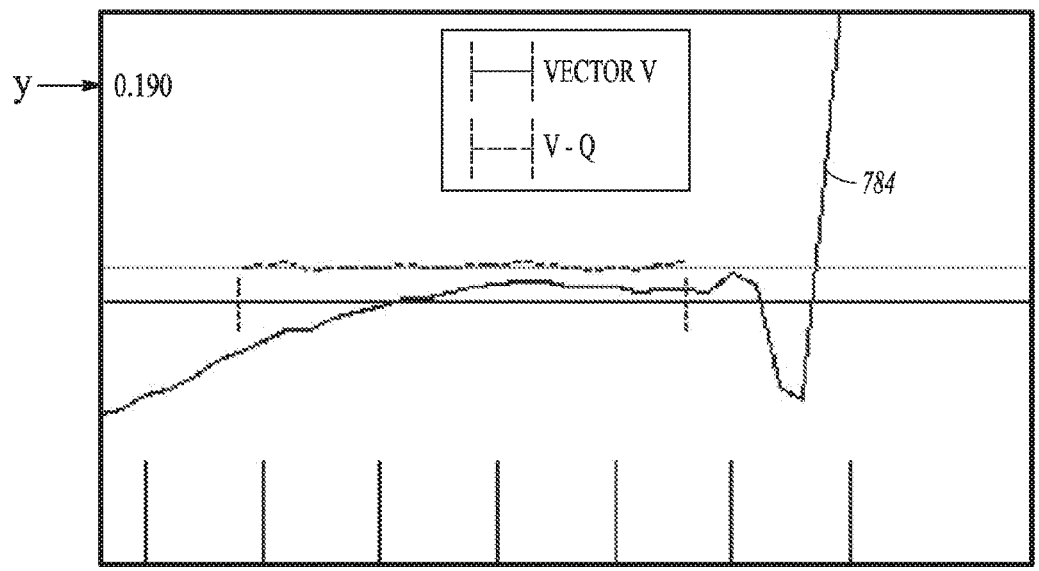
FIG. 7 is an illustration of an example of the vector indicating AF.

At 478, a verified detection of AF is indicated in response to y being less than an atrial activity threshold T, which is an indication of the absence of consistency of each detected ventricular depolarization preceded by an atrial depolarization. The suggested detection of AF is not verified if y is not less than an atrial activity threshold T (i.e., an indication of consistency of each detected ventricular depolarization preceded by an atrial depolarization). FIG. 6 is an illustration of an example of vector $V_i$ indicating a normal sinus rhythm associated with a filtered cardiac signal 684. FIG. 7 is an illustration of an example of vector $V_i$ indicating AF associated with a filtered cardiac signal 784.

In one embodiment, method 470 is performed to time storage of the cardiac signal to allow for analysis of AF at a later time. The indication of a verified detection of AF at 478 triggers storage of the cardiac signal. The storage may end when the detection of AF is no longer suggested at 473 or no longer verified at 478. In another embodiment, method 470 is performed to control delivery of a therapy based on whether a verified detection of AF is indicated at 478.

Figure 8:
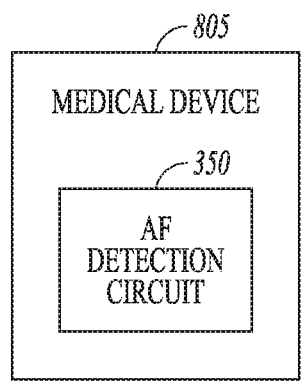
FIG. 8 is a block diagram illustrating an embodiment of a medical device including the AF detection circuit of FIG. 3.

FIG. 8 is a block diagram illustrating an embodiment of a medical device 805 including the AF detection circuit 350. IMD 105 is an example of medical device 805. Other examples of medical device 805 includes an implantable loop recorder (ILR) that senses one or more ventricular signals, a single-chamber ICD in which atrial electrogram is not sensed, diagnostic patches or wearable devices that sense surface ECGs, and subcutaneous devices that are implanted subcutaneously to sense cardiac activities.

In various embodiments, the circuit of medical device 805, including CRM circuit 230 and AF detection circuit 350, may be implemented using a combination of hardware and software. In various embodiments, each element of CRM circuit 230 and AF detection circuit 350, as illustrated in FIGS. 1 and 2, including their various embodiments, may be implemented using an application-specific circuit constructed to perform one or more particular functions or a general-purpose circuit programmed to perform such function(s). For example, control circuit 236, detector 356, and detection enhancer 358 may each be implemented using an application-specific circuit constructed to perform one or more functions discussed as method(s) or method step(s) in this document or a general-purpose circuit programmed to perform such function(s). Such a general-purpose circuit includes, but is not limited to, a microprocessor or a portion thereof, a microcontroller or portions thereof, and a programmable logic circuit or a portion thereof.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for detecting and treating atrial fibrillation (AF), comprising:
    an AF detection circuit including:
        a cardiac signal input configured to receive a cardiac signal indicative of atrial and ventricular depolarizations;
        a detector configured to detect the ventricular depolarizations using the cardiac signal, to measure ventricular intervals each between two successively detected ventricular depolarizations, and to detect AF using the ventricular intervals; and
        a detection enhancer configured to generate atrial detection windows each being a time interval prior to each of the detected ventricular depolarizations, to compute an atrial activity score using a rolling average of portions of the cardiac signal within the atrial detection windows, and to verify the detection of the AF using the atrial activity score and an atrial activity threshold, the atrial activity score being a measure of consistency of each of the detected ventricular depolarizations being preceded by one of the atrial depolarizations.

2. The system of claim 1, wherein the detector is configured to compute a measure of ventricular rate variability using the ventricular intervals and to indicate a suggested detection of AF in response the measure of ventricular rate variability satisfying one or more criteria for AF.

3. The system of claim 1, wherein the detection enhancer is configured to compute the rolling average by filtering the portions of the atrial signal within the atrial detection window using an infinite impulse response (IIR) low-pass filter, to compute the atrial activity score using the portions of the atrial signal filtered for a specified number of the detected ventricular depolarizations, to compare the atrial activity score to the atrial activity threshold, and to indicate a verified detection of AF using an outcome of the comparison.

4. The system of claim 3, wherein the detection enhancer is configured to:
create a vector $V_i$ of a length N, N being a number of samples in each of the atrial detection windows;
initialize all elements of $V_i$;
update each vector value $V_i$ for the each of the detected ventricular depolarizations using a value of sample $S_i$ of the portion of the atrial signal within the each of the atrial detection windows;
compute the atrial activity score y after M R-waves, M related to an aggression parameter of the IIR low-pass filter and being large enough for $V_i$ to saturate; and
indicate the verified detection of AF in response to y being less than the atrial activity threshold.

5. The system of claim 3, comprising an implantable medical device including the AF detection circuit.

6. The system of claim 5, wherein the cardiac signal input is configured to receive a ventricular electrogram as the cardiac signal.

7. The system of claim 5, wherein the cardiac signal input is configured to receive a subcutaneous electrocardiogram as the cardiac signal.

8. The system of claim 5, further comprising:
a therapy device configured to deliver one or more therapies; and
a therapy control circuit configured to control the delivery of the one or more therapies based on whether the detection of the AF is verified.

9. The system of claim 8, wherein the therapy device comprises one or more of a cardiac pacing circuit, a cardioversion defibrillation circuit, a neurostimulation circuit, a drug delivery device, or a biologic therapy device.

10. The system of claim 5, further comprising:
a storage device configured to store the sensed cardiac signal; and
a storage control circuit configured to start storage of the sensed cardiac signal in response to the detection of the AF being verified.

11. A method, comprising:
receiving a cardiac signal indicative of atrial and ventricular depolarizations; and;
detecting atrial fibrillation (AF) using the cardiac signal using an AF detection circuit, including:
detecting the ventricular depolarizations using the cardiac signal using a detector of the AF detection circuit;
measuring ventricular intervals each between two successively detected ventricular depolarizations using the detector;
detecting atrial fibrillation (AF) using the ventricular intervals using the detector;
generating atrial detection windows each being a time interval prior to each of the detected ventricular depolarizations using a detection enhancer of the AF detection circuit;
computing an atrial activity score using a rolling average of portions of the cardiac signal within the atrial detection windows using the detection enhancer, the atrial activity score being a measure of consistency of each of the detected ventricular depolarizations being preceded by one of the atrial depolarizations; and
verifying the detection of the AF using the atrial activity score and an atrial activity threshold using the detection enhancer.

12. The method of claim 11, wherein detecting the AF using the ventricular intervals comprises:
computing a measure of ventricular rate variability using the ventricular intervals; and
indicating a suggested detection of AF in response the measure of ventricular rate variability satisfying one or more criteria for AF.

13. The method of claim 11, wherein computing the atrial activity score comprises:
filtering the portions of the atrial signal within the atrial detection window using an infinite impulse response (IIR) low-pass filter; and
computing the atrial activity score using the portions of the atrial signal filtered for a specified number of the detected ventricular depolarizations.

14. The method of claim 13, wherein generating the atrial detection windows comprises generating the atrial detection windows each starting at about 160 to 400 milliseconds before the each of the detected ventricular depolarizations and ending at about 40 to 100 milliseconds before the each of the detected ventricular depolarizations.

15. The method of claim 13, wherein filtering the portions of the atrial signal within the atrial detection window using an IIR low-pass filter comprises:
creating a vector $V_i$ of a length N, N being a number of samples in each of the atrial detection windows;
initializing all elements of $V_i$; and
updating each vector value $V_i$ for the each of the detected ventricular depolarizations using a value of sample $S_i$ of the portion of the atrial signal within the each of the atrial detection windows.

16. The method of claim 15, wherein updating the each vector value $V_i$ for the each of the detected ventricular depolarizations comprises updating the each vector value $V_i$ for the each of the detected ventricular depolarizations using:

$$V_i = \alpha V_i + (1-\alpha) S_i,$$

where $\alpha$ is the aggression parameter of the IIR low-pass filter.

17. The method of claim 15, wherein computing the atrial activity score comprises computing the atrial activity score y after M R-waves, M related to an aggression parameter of the IIR low-pass filter and being large enough for $V_i$ to saturate.

18. The method of claim 17, wherein computing the atrial activity score comprises computing the atrial activity score using:

$$y = \sum_N |V_i - Q_i|,$$

where $Q_i$ is a function numerically fitted to $V_i$ to compensate for short-term baseline fluctuation in the cardiac signal.

19. The method of claim 17, wherein verifying the detection of the AF comprises indicating a verified detection of AF in response to y being less than the atrial activity threshold.

20. The method of claim 11, further comprising triggering storage of the sensed cardiac signal in response to the detection of the AF being verified.

* * * * *